United States Patent
Schmenger et al.

(10) Patent No.: US 9,795,547 B2
(45) Date of Patent: Oct. 24, 2017

(54) HAIR TREATMENT COMPOSITION, KIT AND METHOD THEREOF

(71) Applicant: Noxell Corporation, Hunt Valley, MD (US)

(72) Inventors: Jurgen Schmenger, Darmstadt (DE); Andrei Sergeevich Bureiko, Cincinnati, OH (US)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 14/799,042

(22) Filed: Jul. 14, 2015

(65) Prior Publication Data

US 2016/0008242 A1    Jan. 14, 2016

(30) Foreign Application Priority Data

Jul. 14, 2014 (EP) .................................... 14176851
Jun. 12, 2015 (EP) .................................... 15171788

(51) Int. Cl.

| | |
|---|---|
| *A61Q 5/10* | (2006.01) |
| *A61Q 5/08* | (2006.01) |
| *A61Q 5/12* | (2006.01) |
| *A61K 8/22* | (2006.01) |
| *A61K 8/41* | (2006.01) |
| *A61K 8/34* | (2006.01) |
| *A61K 8/19* | (2006.01) |
| *A61K 8/92* | (2006.01) |

(52) U.S. Cl.
CPC ................ *A61K 8/342* (2013.01); *A61K 8/19* (2013.01); *A61K 8/22* (2013.01); *A61K 8/34* (2013.01); *A61K 8/92* (2013.01); *A61Q 5/08* (2013.01); *A61Q 5/10* (2013.01); *A61Q 5/12* (2013.01); *A61K 2800/4324* (2013.01); *A61K 2800/882* (2013.01)

(58) Field of Classification Search
CPC ...... A61K 2800/882; A61K 2800/4324; A61K 8/22; A61Q 5/10; A61Q 5/065; A61Q 5/08; A61Q 5/12
See application file for complete search history.

(56) References Cited

U.S. PATENT DOCUMENTS

| | | | |
|---|---|---|---|
| 7,887,600 B2 | 2/2011 | Bureiko | |
| 8,585,777 B2 | 11/2013 | Misu | |
| 8,956,599 B2 | 2/2015 | Caballero | |
| 2002/0139957 A1* | 10/2002 | Matsuo | A61K 8/22 252/186.1 |
| 2003/0190297 A1 | 10/2003 | Narasimhan | |
| 2003/0226217 A1 | 12/2003 | Bowes | |
| 2004/0064903 A1 | 4/2004 | Massoni | |
| 2004/0141931 A1 | 7/2004 | Narasimhan et al. | |
| 2007/0048241 A1 | 3/2007 | Obukowho | |
| 2007/0209124 A1 | 9/2007 | Bureiko | |
| 2008/0010754 A1 | 1/2008 | Bureiko | |
| 2011/0067723 A1 | 3/2011 | Bureiko | |
| 2011/0253163 A1* | 10/2011 | Balakrishnan | A61K 8/19 132/208 |
| 2013/0167863 A1* | 7/2013 | Schmelz | A61K 8/0241 132/208 |
| 2014/0165299 A1 | 6/2014 | Neuba | |
| 2014/0165300 A1 | 6/2014 | Neuba | |

FOREIGN PATENT DOCUMENTS

| | | |
|---|---|---|
| EP | 1832273 A1 | 9/2007 |
| EP | 1878469 A1 | 1/2008 |
| EP | 2308564 A1 | 4/2011 |
| JP | 2008143829 A | 6/2008 |
| JP | 2008156252 A | 7/2008 |
| JP | 2008290971 A | 12/2008 |
| WO | 2014090645 A2 | 6/2014 |
| WO | 2015018412 A2 | 2/2015 |
| WO | WO-2016010982 A1 | 1/2016 |

OTHER PUBLICATIONS

"European Application Serial No. 15171788.1, Extended European Search Report mailed Sep. 28, 2015", 5 pgs.
"International Application Serial No. PCT/US2015/040311, International Preliminary Report on Patentability mailed Jan. 26, 2017", 7 pgs.
"International Application Serial No. PCT/US2015/040311, International Search Report mailed Sep. 16, 2015", 3 pgs.
"International Application Serial No. PCT/US2015/040311, International Search Report mailed Sep. 16, 2015", 5 pgs.
International Search Report and Written Opinion, PCT/US2015/040311, date of mailing Sep. 16, 2015.

\* cited by examiner

*Primary Examiner* — Tracy Liu
(74) *Attorney, Agent, or Firm* — Schwegman Lundberg & Woessner P.A.

(57) ABSTRACT

A hair treatment composition, particularly a hair coloring and/or bleaching composition, comprising one or more oxidizing agent(s), one or more alkalizing agent(s) selected from the group consisting of ammonia, its salts and mixtures thereof, one or more fatty alcohol(s), one or more non-ionic surfactant(s) and a low amount of specific fatty compound(s). It is also provided a kit and method thereof. Superior hair treatment performance, particularly superior coloring and bleaching performance, with a reduced or an eliminated smell of said alkalizing agent(s) upon application, is achieved.

19 Claims, No Drawings

HAIR TREATMENT COMPOSITION, KIT AND METHOD THEREOF

FIELD OF THE INVENTION

The present invention relates to a hair treatment composition, particularly a hair colouring and/or bleaching composition, comprising an alkalizing agent selected from the group consisting of ammonia, its salts and mixtures thereof, one or more fatty alcohol(s), one or more non-ionic surfactant(s) different from fatty alcohol(s) and a low amount of (or even no) fatty compound(s). It also relates to kit and method thereof. The present invention provides superior hair treatment performance, particularly superior colouring and bleaching performance, with a reduced or an eliminated smell of said alkalizing agent upon application.

BACKGROUND OF THE INVENTION

The permanent alteration of the colour of keratinous fibers, in particular human hair, by the application of hair dyes is well known. In order to provide the consumer with the hair colour and the intensity of the colour desired, very complex chemical processes are utilized. Permanent hair colouring formulations typically comprise oxidative hair dye precursors, which can diffuse into the hair through the cuticle and into the cortex where they can then react with each other and suitable oxidizing agents to form the end dye molecule. Due to the larger size of these resultant molecules they are unable to readily diffuse out of the hair during subsequent washing with water and/or detergent; hence delivering a consumer-desired permanency of colour. This reaction typically takes place at pH from about 8.5 to about 10.5 (approximately pH 10) in the presence of an alkalizing agent and an oxidizing agent.

Despite the fact that commercial hair colouring products have been available for many years, the products still exhibit a number of consumer-related deficiencies.

Typically, permanent hair dye products will contain an alkali, typically a source of ammonia. This serves the purpose of swelling the hair allowing the entry of the dye precursor molecules into the hair and also improves the lightening effect of the oxidizing agent, which is typically hydrogen peroxide. Ammonia shows the best hair colouring and/or bleaching performance as well as hair damage profile, versus alternative alkalizing agents. However, ammonia is also volatile and its associated odour is extremely unpleasant to the consumers of such products, particularly as these hair colouring and/or bleaching products are used in close proximity to the nasal region. Hence, it would be highly desirable to provide an oxidative hair colouring and/or bleaching composition, and kit thereof, which delivers the consumer required lightening level and colour but which has reduced or eliminated the detectable ammonia odour.

A number of attempts have been described in the literature to address the above identified improvement areas. For example, it has been described hair colouring and/or bleaching compositions comprising carbonate and/or carbamate compounds. It has also been described hair colouring and/or bleaching compositions comprising an alkalizing agent, alternative to ammonia and its salts, such as monoethanolamine. It has also been described compounds blocking and/or antagonizing the odour of ammonia. Furthermore, compositions comprising a certain level of fatty compound have also been developed. However these previous attempts have not proven fully satisfactory vis-à-vis further criteria, as they may exhibit a limited hair colouring and/or bleaching performance including limited colour delivery, uptake and/or durability; significant damages to the hair including brittle fibre formation and/or impart a greasy feeling to hair when the composition is applied onto hair. In some embodiments, the use of fatty compounds in the compositions may have further disadvantages, e.g. the process for making the compositions may be more complex and the compositions may have a weaker stability at high temperatures.

Compositions with reduced ammonia smell have been disclosed in WO 2014/090645 A2, US 2014/0165299 A1, US 2014/0165300 A1 and WO 2015/018412 A2.

However, there is still the need for providing a composition comprising ammonia and/or its salts thereof, which releases a reduced or no odour, especially upon application onto hair. There is also the need for providing a composition comprising ammonia and/or its salts thereof, which releases a reduced or no odour, while providing superior hair treatment performance. There is also the need for providing a composition comprising ammonia and/or its salts thereof, releasing a reduced or no odour, without imparting significant damages onto the hair fibers. There is also the need for providing a composition comprising ammonia and/or its salts thereof releasing a reduced or no odour, without imparting a greasy feeling to hair. Finally, there is also the need for providing a composition comprising ammonia and/or its salts thereof releasing a reduced or no odour which is easy to make and is characterized by a good stability at high temperatures.

SUMMARY OF THE INVENTION

In one aspect, the present invention relates to a hair colouring and/or bleaching composition comprising a first aqueous component and a second aqueous component, mixed prior to application onto hair. The first aqueous component comprises, in a cosmetically acceptable carrier one or more oxidizing agent(s); optionally one or more fatty alcohol(s) and optionally one or more non-ionic surfactant(s) other than fatty alcohol(s). The second aqueous component comprises, in a cosmetically acceptable carrier one or more alkalizing agent(s) selected from the group consisting of ammonia, its salts and mixtures thereof; one or more fatty alcohol(s); one or more non-ionic surfactant(s) other than fatty alcohol(s). The ratio between the total amount of fatty alcohol(s) and the total amount of non-ionic surfactant(s) other than fatty alcohol(s) comprised in the composition ranges from 10:0.1 to 10:4.2. The composition comprises a total amount of fatty compound(s) selected from the group consisting of mineral oil, hydrocarbon oil, and mixtures thereof of less than 1% by total weight of the composition. The composition comprises a total amount of anionic surfactant(s) of less than 0.5% by total weight of the composition and a total amount of cationic surfactant(s) of less than 0.5% by total weight of the composition.

In another aspect, the present invention relates to a hair colouring and/or bleaching kit. In another aspect, the present invention relates to a method for colouring and/or bleaching hair.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred.

However wool, fur and other keratin containing fibers are suitable substrates for the compositions according to the present invention.

By "hair colouring" composition, it is meant a composition suitable for changing the colour of hair. The hair colouring composition is referred hereinafter as "the composition", unless otherwise specified. The hair colouring composition may comprise oxidative dye precursors, direct dyes or even no, or substantially no, dyes in case of bleaching only compositions where the change of colour is mainly caused by the degradation of the natural melanin contained in the hair shaft by the oxidizing agent. The term "hair colouring" composition as used herein covers hair bleaching and hair oxidative dyeing products.

By "fatty alcohol" it is meant a non-alkoxylated, saturated or unsaturated, linear or branched alcohol having from 14 to 30 carbon atoms.

All percentages are by weight of the hair colouring composition, i.e. of the ready-to-use composition which is the composition to be applied on hair, unless otherwise specified. When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

The present invention relates to a hair colouring and/or bleaching composition comprising a first aqueous component and a second aqueous component, said first and second aqueous components being mixed prior to application onto hair. The first aqueous component, also called developer component or oxidizing component, comprises, in a cosmetically acceptable carrier, one or more oxidizing agent(s) and optionally one or more fatty alcohol(s) and/or one or more non-ionic surfactant(s) other than fatty alcohol(s). The second aqueous component, also called tint component or dye component, comprises, in a cosmetically acceptable carrier, one or more alkalizing agent(s) selected from the group consisting of ammonia, its salts and mixtures thereof and one or more fatty alcohol(s) and one or more non-ionic surfactant(s) other than fatty alcohol(s).

The ratio between the total amount of fatty alcohol(s) and the total amount of non-ionic surfactant(s) other fatty alcohol(s) comprised in the composition ranges from 10:0.1 to 10:4.2, alternatively from 10:0.1 to 10:4.1, alternatively from 10:0.1 to 10:4, alternatively from 10:0.5 to 10:3.5, alternatively from 10:1 to 10:2.

The ratio between the total amount of fatty alcohol(s) and the total amount of non-ionic surfactant(s) other than fatty alcohol(s) comprised in the second aqueous component ranges from 10:0.1 to 10:4.5 alternatively from 10:0.1 to 10:4, alternatively from 10:1 to 10:4, alternatively from 10:1 to 10:3.

The first and the second components may be mixed prior to application to hair in a ratio ranging from 5:1 to 1:5, alternatively from 3:1 to 1:3, alternatively from 2:1 to 1:2, alternatively in a ratio of 1:1.

The composition comprises one or more fatty alcohol(s). The fatty alcohol(s) may be selected from the group consisting of linear and/or branched C14 to C30 fatty alcohols; alternatively from the group consisting of C14 to C30 fatty alcohols; alternatively from the group consisting of cetyl alcohol, stearyl alcohol, cetearyl alcohol, behenyl alcohol, any mixtures thereof. The composition may comprise a total amount of fatty alcohol(s) ranging from 0.5% to 20%, alternatively from 2% to 10%, alternatively from 4% to 8%, by total weight of the composition. The amount of each particular fatty alcohol or mixtures thereof described hereinbefore can account for up to 100% (or 100%) of the total amount of fatty alcohol(s) in the composition.

The composition comprises one or more non-ionic surfactant(s) other than fatty alcohol(s). The non-ionic surfactant(s) may be selected from non-ionic surfactant(s) comprising one or more polyethyleneoxide chain including the following compounds: polyoxyethylene alkyl ethers, polyethyleneglycol fatty acid esters, polyoxyethylene castor oil, polyoxyethylene hydrogenated castor oil, polyoxyethylene fatty amides and their monoethanolamine and diethanolamine derivatives and polyethoxylated fatty amines, and mixtures thereof.

The non-ionic surfactant(s) may be selected from the group consisting of polyoxyethylene C8 to C30 alkyl ethers; alternatively from the group consisting of polyoxyethylene C8 to C30 alkyl ethers having at least 5 ethylene oxide units, or at least 10 ethylene oxide units, or at least 20 ethylene oxide units; alternatively from the group consisting of polyoxyethylene C8 to C30 alkyl ethers having from 10 to 200 ethylene oxide units; alternatively from the group consisting of polyoxyethylene C8 to C30 alkyl ethers having from 20 to 200 ethylene oxide units; alternatively from the group consisting of ceteareth-25, steareth-20, steareth-100, steareth-150, steareth-200, and mixtures thereof.

Alternatively, the non-ionic surfactant(s) may be free of polyethyleneoxide chains. Representative examples of non-ionic surfactants free of polyethyleneoxide chains include polyglycerolated fatty acids, polyglycerolated fatty amides, polyglycerolated alkyl phenols, polyglycerolated [alpha]-diols, polyglycerolated alcohols, alkyl polyglucosides, sugar esters and mixtures thereof.

The composition may comprise a total amount of non-ionic surfactant(s) other than fatty alcohol(s) ranging from 0.2% to 5%, alternatively from 0.5% to 3%, alternatively from 0.7% to 1.5% by total weight of the composition. The amount of each particular non-ionic surfactant or mixtures thereof described hereinbefore can account for up to 100% (or 100%) of the total amount of non-ionic surfactant(s) in the composition.

The composition may comprise a total amount of fatty alcohol(s) and non-ionic surfactant(s) ranging from 1% to 30%, alternatively from 1.5% to 15% by total weight of the composition.

The fatty alcohol(s) and the non-ionic surfactant(s) may be comprised in the composition, in part or all, in a gel network system. The fatty alcohol(s) and the non-ionic surfactant(s) may be comprised in the first and/or the second aqueous component(s), in part or all, in a gel network system.

The formation of the gel network involves heating a dispersion of the fatty alcohol(s) in water with the surfactant(s) to a temperature above 80° C. During the mixing process, the fatty alcohol(s) melts, allowing the surfactant(s) to partition into the fatty alcohol(s) droplets. The surfactant(s) brings water along with it into the fatty alcohol(s). This changes the isotropic fatty alcohol(s) drops into liquid crystalline phase drops. When the mixture is cooled below the chain melt temperature the liquid crystal phase is converted into a solid crystalline gel network. The gel network may contribute in reducing, or even eliminating, the ammonia odour.

From 50% to 100%, alternatively from 70% to 100%, alternatively from 90% to 100%, alternatively substantially 100% of the fatty alcohol(s) present in the composition may be comprised within the gel network. From 50% to 100%, alternatively from 70% to 100%, alternatively from 90% to 100%, alternatively substantially 100% of the non-ionic surfactant(s) present in the composition may be comprised within the gel network.

The composition comprises a total amount of fatty compound(s) selected from the group consisting of mineral oil, hydrocarbon oil, and mixtures thereof of less than 1%, alternatively less than 0.5% by total weight of the composition. Commercially suitable raw materials include materials of the Marcol™ Series from ExxonMobile, particularly Marcol™ 52 and Marcol™ 82. The amount of each particular fatty compound or mixtures thereof described hereinbefore can account for up to 100% (or 100%) of the total amount of fatty compound(s) in the composition. The inventors have surprisingly found that the ammonia odour, which is particularly noticeable during application and leave of the hair colouring and/or bleaching composition onto hair, can be significantly reduced, or even eliminated, by carefully selecting and using in combination specific classes of compounds. Indeed, the inventors have found that the reduction or elimination of smell is achieved with fatty alcohol(s) and non-ionic surfactant(s), wherein the fatty alcohol(s) and the non-ionic surfactant(s) are comprised in the composition at a specific ratio. They have surprisingly found that the reduction or elimination of smell can even be achieved using a low amount of fatty compound(s) or even without using fatty compound(s) selected from the group consisting of mineral oil, hydrocarbon oil, and mixtures thereof, i.e. without imparting a greasy feeling to hair or making the process for making these compositions more complex or reducing the stability of the compositions at high temperatures.

It has also been found that the colouring and/or bleaching performance—including colour delivery, uptake and durability—was not impaired, and that the composition does not damage hair fibers further versus conventional ammonia-containing compositions.

The composition according to the present invention further comprises one or more oxidizing agent(s). Any oxidizing agent known in the art may be used. Preferred oxidizing agent(s) are water-soluble peroxygen oxidizing agent(s). As used herein, "water-soluble" means that in standard conditions at least 0.1 g, preferably 1 g, more preferably 10 g of the oxidizing agent can be dissolved in 1 liter of deionized water at 25° C. The oxidizing agent(s) are valuable for the initial solubilisation and decolorisation of the melanin (bleaching) and accelerate the oxidation of the oxidative dye precursors (oxidative dyeing) in the hair shaft.

Suitable water-soluble oxidizing agent(s) include, but are not limited to: inorganic peroxygen materials capable of yielding hydrogen peroxide in an aqueous solution. Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agent(s) may be provided in aqueous solution or as a powder which is dissolved prior to use.

In a specific embodiment, the composition comprises water-soluble oxidizing agent(s) selected from the group consisting of hydrogen peroxide, percarbonates (which may be used to provide a source of both oxidizing agent and carbonate ions and or ammonium ions), persulphates, and mixtures thereof; alternatively a water-soluble oxidizing agent being hydrogen peroxide.

The composition may comprise a total amount of oxidizing agent(s) ranging from 0.1% to 10%, alternatively from 1% to 7%, alternatively from 2% to 5%, by total weight of the composition. The amount of each particular oxidizing agent or mixtures thereof described hereinbefore can account for up to 100% (or 100%) of the total amount of oxidizing agent(s) in the composition. The composition comprises one or more an alkalizing agent(s), wherein the alkalizing agent(s) is selected from the group consisting of ammonia, its salts and mixtures thereof; alternatively from the group consisting of ammonia, ammonium halides, ammonium sulfate, ammonium phosphate, ammonium lactate, ammonium glycinate, ammonium aspartate, ammonium nitrate, ammonium perchlorate, ammonium carbonate, ammonium hydrogen carbonate, ammonium silicate, ammonium borate, and mixtures thereof; alternatively from the group consisting of ammonia, ammonium carbonate, and mixtures thereof; alternatively wherein the alkalizing agent is ammonia; alternatively wherein the alkalizing agent is ammonium carbonate. If present, the ammonium ions and the carbonate ions are present in the composition at a weight ratio of from 3:1 to 1:10, alternatively from 2:1 to 1:5.

The composition may comprise a total amount of alkalizing agent(s) ranging from 0.1% to 10%, alternatively from 0.5% to 6%, alternatively from 1% to 4%, by total weight of the composition. The amount of each particular alkalizing agent or mixtures thereof described hereinbefore can account for up to 100% (or 100%) of the total amount of alkalizing agents in the composition.

The composition comprises a cosmetically acceptable carrier or solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglycol, polyglycerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least 50%, alternatively from at least 60%, alternatively from at least 70%, by total weight of the composition. Typically, when present, the composition comprises a total amount of organic solvents ranging from 1% to 30%, by total weight of the composition.

The composition may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the composition may comprise a total amount of oxidative dye precursors ranging up to 12%, alternatively from 0.1% to 10%, alternatively from 0.3% to 8%, alternatively from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis (azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The composition may further comprise compatible direct dyes, in an amount sufficient to provide additional coloring, particularly with regard to intensity. Typically, the composition may comprise a total amount of direct dyes ranging from 0.05% to 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

The composition may further comprise one or more chelant(s) (also known as "chelating agent", "sequestering agent", or "sequestrant") in an amount sufficient to reduce the amount of metals available to interact with formulation components, particularly oxidizing agents, more particularly peroxides. Any suitable chelant known in the art may be used.

The composition may comprise a total amount of chelant(s) ranging from at least 0.01%, alternatively from 0.01% to 5%, alternatively from 0.25% to 3%, alternatively from 0.5% to 1%, by total weight of the composition.

Suitable chelant(s) include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

The composition may comprise chelant(s) selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

The composition may further comprise one or more radical scavenger(s). As used herein the term "radical scavenger" refers to a species that can react with a radical, preferably a carbonate radical to convert the radical species by a series of fast reactions to a less reactive species. In one embodiment, the radical scavenger(s) is different from the alkalising agent and/or is present in an amount sufficient to reduce the damage to the hair during the colouring/bleaching process.

The composition may comprise a total amount of radical scavenger(s) ranging from 0.1% to 10%, alternatively from 1% by weight to 7%, by total weight of the composition.

Suitable radical scavenger(s) includes, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

The composition may further have a pH of from 3 to 13, alternatively from 8 to 12, alternatively from 9 to 11. The composition may also comprise, in addition to the alkalizing agent(s) discussed above, pH modifier(s) and/or buffering agent(s) in an amount that is sufficiently effective to adjust the pH of the composition to fall within a range from 3 to 13, alternatively from 8 to 12, alternatively from 9 to 11.

Suitable pH modifier(s) and/or buffering agent(s) include, but are not limited to: ammonia; alkanol amides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifier(s) and/or buffering agent(s) include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

The composition may further comprise thickener(s) and/or rheology modifier(s) in an amount sufficient to provide the composition with a viscosity so that it can be readily applied to the hair without unduly dripping off the hair and causing mess.

The composition may comprise a total amount of thickener(s) ranging from at least 0.1%, alternatively at least 0.5%, alternatively at least 1%, by total weight of the composition.

Suitable thickener(s) include, but are not limited to: associative polymers, polysaccharides, non-associative polycarboxylic polymers, and mixtures thereof. Commercially available salt-tolerant thickeners include, but not limited to: xanthan, guar, hydroxypropyl guar, scleroglucan, methylcellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrollidone (Povidone), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Di-cetyl phosphate and Cetearyl alcohol (available as Crodafos CES), and mixtures thereof. The composition may comprise a total amount of thickener(s) selected from anionic and cationic polymer(s) of less than 1%, alternatively less than 0.1% by total weight of the composition.

The composition may further comprise a source of carbonate ions, carbamate ions, hydrogen carbonate ions, and mixtures thereof in a sufficient amount to reduce damage to the hair during the coloring process.

The composition may comprise a total amount of a carbonate ion source ranging from 0.1% to 15%, alternatively from 0.1% to 10%, alternatively from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

The composition may further comprise one or more conditioning agent(s), and/or be used in combination with a composition comprising one or more conditioning agent(s). Any suitable conditioning agent(s) known in the art may be used.

The composition may comprise a total amount of conditioning agent(s) ranging from 0.05% to 20%, alternatively from 0.1% to 15%, alternatively from 0.2% to 10%, alternatively from 0.2% to 2%, alternatively from 0.5% to 2%, by total weight of the composition. The conditioning agent(s) may be included in a separate pre- and/or post-treatment composition.

Suitable conditioning agent(s) include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agent(s) include mineral oils and other oils such as glycerin and sorbitol. The composition may comprise a total amount of cationic conditioning agent(s) of less than 1%, alternatively less than 0.1% by total weight of the composition.

The composition may further comprise surfactant(s), other than the non-ionic surfactant(s). Suitable surfactant(s) generally have a lipophilic chain length of from 8 to 30 carbon atoms and can be selected from anionic surfactants, amphoteric surfactants, cationic surfactants, and mixtures thereof. Any suitable surfactant(s) known in the art may be used.

The composition comprises a total amount of anionic surfactant(s) of less than 0.5%, alternatively less than 0.3%, alternatively less than 0.1% by total weight of the composition. Alternatively, the composition may be free of anionic surfactant(s).

The composition comprises a total amount of cationic surfactant(s) of less than 0.5%, alternatively less than 0.3%, alternatively less than 0.1% by total weight of the composition. Alternatively, the composition may be free of cationic surfactant(s).

The composition may comprise a total amount of anionic surfactant(s) of less than 0.3% by total weight of the composition and a total amount of cationic surfactant(s) of less than 0.3% by total weight of the composition.

The composition may comprise a total amount of anionic surfactant(s) of less than 0.1% by total weight of the composition and a total amount of cationic surfactant(s) of less than 0.1% by total weight of the composition.

The composition may be free of anionic surfactant(s) and free of cationic surfactant(s). The inventors have surprisingly found that a greater reduction of ammonia odour is achieved when the hair colouring and/or bleaching composition is free of anionic and/or cationic surfactant(s). Indeed, it is believed that incorporating anionic and/or cationic surfactant(s) into the composition may alter the gel network formation, the presence of said gel network—being necessary for achieving the ammonia odour reduction upon application onto hair.

The composition may comprise a total amount of surfactant(s) other than fatty alcohol(s) and non-ionic surfactant(s) of less 1%, alternatively less than 0.5%, alternatively less than 0.3%, alternatively less than 0.1% by total weight of the composition.

The composition may comprise, in addition to the ingredients indicated above, further ingredients in order to further enhance the properties of the composition, as long as these are not excluded by the claims. Suitable further ingredients include, but not limited to: solvents; peroxymonocarbonate ion sources; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

The composition may be free of amine compounds and/or phospholipid compounds; alternatively may be free of fatty monoamine compounds, polyamine compounds having at least three amino groups and fatty quaternary amine compounds and/or phospholipid compounds.

The composition may comprise a total amount of polymer(s) selected from anionic and cationic polymer(s) of less than 1%, alternatively less than 0.1% by total weight of the composition. Alternatively, the composition may be free of anionic and cationic polymer(s).

The composition may have viscosity of from 1000 to 60000 cPs, alternatively from 2000 to 30000 cPs, alternatively from 3000 to 25000 cPs. Viscosity is measured using Brookfield viscometers with cone and plate attachment. For viscosities in the range of 0 to 12000 cPs, the Brookfield DV-11 viscometer with S42 plate is used. 2 ml sample of the composition is equilibrated at 26.7° C. for three minutes before the readings are taken at 1 rpm. For viscosities in the range of 12,000 to 60,000 cPs, the Brookfield DV-1 viscometer with S52 plate is used. 0.5 ml sample of the composition is equilibrated for 1 minute at 26.7° C. before the readings are taken at 1 rpm.

The compositions may be provided in the form of foam which is applied to the hair. Foam formation is typically achieved by the use of a foaming agent incorporated within the mixed composition (typically present in either the oxidizing composition or the dye composition or both) in combination with a manually operated foaming device. Such manually operated foaming devices are known in the art and include aerosols devices, squeeze foamers and pump foamers. Suitable foaming agents includes surfactants such as anionic, nonionic and amphoteric surfactants, nonionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

The oxidizing agent(s), the alkalizing agent, the fatty alcohol(s), the non-ionic surfactant(s), the fatty compound(s) and the cosmetically acceptable carrier, to be incorporated into the first and/or the second component, have been defined hereinbefore. Likewise, any suitable optional compounds including the oxidative dye precursor(s), the direct dye(s), the chelant(s), the radical scavenger(s), pH modifier(s) and/or buffering agent(s), thickener(s) and/or rheology modifier(s), carbonate ion source(s), conditioning agent(s), surfactant(s), and any further ingredients, to be incorporated into the first and/or the second composition, have also been defined hereinbefore. The first and the second components may be mixed for 5 sec to 3 min, alternatively for 15 sec to 2 min, alternatively for 30 sec to 1 min.

Depending on stability and reactivity considerations, the compounds may be incorporated indifferently into the first and/or the second components, or may preferably be incorporated into one of the two components. The fatty compound(s) selected from the group consisting of a mineral oil, hydrocarbon oil, and mixtures thereof when present may be incorporated into the first component, the second component being free of said fatty compound. The fatty alcohol(s) and/or the non-ionic surfactant(s) may be incorporated into the first component and/or the second component.

The oxidative dye precursors including the primary intermediates and couplers are usually incorporated into the second component. The direct dyes are usually incorporated into the second component. The chelant may be incorporated into the first and/or the second component, however the chelant is usually incorporated into the first component for stability reason.

In another aspect, the present invention relates to a kit for colouring and/or bleaching hair comprising an individually packaged first component and an individually packaged second component. Individually packaged components mean that they may be packaged in separate containers or in compartmented containers. The consumer mixes the first component and the second component together immediately before use and applies it onto the hair. The first and the second components may be mixed from 5 sec to 3 min, alternatively from 15 sec to 2 min, alternatively for 30 sec to 1 min prior application to the hair.

After working the combined mixture for a few minutes (to insure uniform application to all of the hair), the hair colouring and/or bleaching composition is allowed to remain on the hair for an amount sufficient for the dyeing to take place, usually from 2 min to 60 min, typically from 30 min to 45 min. The consumer or salon professional then rinses the hair thoroughly with water and/or shampoo and allows it to dry. It will be observed that the hair has changed from its original colour to the desired colour.

The kit may also comprise a third component selected from the group consisting of a conditioning composition, a pre-treatment composition, and/or a colour refresher composition. The pre-treatment may be applied onto hair, before applying the hair colouring and/or bleaching composition. The conditioning composition, comprising a conditioning agent, may be mixed together with the first and the second component prior to application onto hair, or may be alternatively applied separately onto hair, for example after applying the hair colouring and/or bleaching composition. The colour refresher composition, comprising optionally a pre-formed dye, may be applied after applying the hair colouring and/or bleaching composition. The component could be also a carrier for dye precursors or concentrates.

In another aspect, the present invention relates to a method of colouring and/or dyeing hair comprising applying onto hair a hair colouring and/or bleaching composition as defined herein before. The method may comprise the steps of: providing a first component as defined hereinbefore; providing a second component as defined hereinbefore; mixing the first and the second components for obtaining a hair colouring and/or bleaching composition; applying the obtained composition onto hair; optionally leaving the applied composition on hair from 5 min to 60 min, alternatively 10 min to 30 min; optionally rinsing hair using a rinsing composition, alternatively rinsing hair with water; optionally cleansing hair using a cleansing composition; optionally treating hair with a conditioning and/or treating composition; and, optionally drying hair.

The kits described hereinabove are well-known in the art and the compositions in each container can be manufactured utilizing any one of the standard approaches, these include a) 'Oil-in-water' process, b) 'Phase Inversion' process and c) 'One-pot' process. For example, when using "oil-in-water" process, surfactants of the present invention are added to approximately 50% of total water amount of the composition at 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or colouring kit.

The present invention may be provided in a variety of packaging devices and/or dispensing devices. These dispensing devices can come in the form of separate devices which may be used independently or in combination with one another. Typically, the hair colouring and/or bleaching compositions are contained within separate single or multi-compartment containers so that the compositions can be stored separately from one another before use. The compositions are then mixed together by a mixing means and then dispensed from the device and applied to the consumer's hair by an application means.

The most common packaging device which can be used involves storing the developer component in a container such as a bottle, tube, aerosol, or a sachet and separately storing the dye component in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the developer component and the tint component by any means, including by using a mixing bowl and/or a mixing tool, by adding one component into the container of the other component followed by mixing, or by performing or displacing a seal located between the separate compartments of the components within a single container or sachet followed by mixing.

The devices described herein above can also be used in combination with a product delivery and or application tool to aid application of the product onto the hair, including using a nozzle attached to one of the containers, using a separate applicator device such as a comb or brush, using a comb attached to or instead of the dispensing nozzle whereby the product is dispensed through hollow tines and dispensing apertures located in the comb tines. The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used. Additional device technology can be used to assist in the penetration of the product into the hair. Examples of such technology include heating devices, ultraviolet light devices and ultrasound devices.

The hair colouring and/or bleaching composition, and the corresponding first and second components, may be manufactured by conventional processes known in the art for manufacturing oxidative hair colouring and/or bleaching products, and ad-mixing the ingredients of each component composition in suitable vessels, followed by packaging in appropriate individual containers.

EXAMPLES

Hair colouring and/or bleaching compositions—Ammonia smell detection—Detection upon application of the hair colouring and/or bleaching composition onto hair fibers.

The following compositions have been prepared.

| Developer | D1 |
| --- | --- |
| Cetearyl alcohol* | 3.4 |
| Ceteareth-25** | 0.8 |
| Etidronic acid, 85% | 0.01 |
| Phosphoric acid, 85% | 0.1 |
| Salicylic acid | 0.1 |
| Disodium phosphate | 0.08 |
| Hydrogen peroxide, 50% | 18.0 |
| Water | Qsp |

|  | Tint | | | | | | | |
| --- | --- | --- | --- | --- | --- | --- | --- | --- |
|  | T1 | T2 | T3 | T4 | T5 | T6 | T7 | T8 |
| Cetearyl alcohol* | 10.0 | 10.0 | 10.0 | 10.0 | 10.0 | 10.0 | 10.0 | 10.0 |
| Steareth-20** | 10.0 | 8.0 | 6.0 | 5.0 | 4.0 | 3.0 | 2.0 | 1.0 |
| Ammonium hydroxide, 25% | 8.0 | 8.0 | 8.0 | 8.0 | 8.0 | 8.0 | 8.0 | 8.0 |
| Water | Qsp | Qsp | Qsp | Qsp | Qsp | Qsp | Qsp | Qsp |

|  | Tint | | |
| --- | --- | --- | --- |
|  | T8 + 0.35% SLES | T8 + 0.7% SLES | T8 + 1.4% SLES |
| Cetearyl alcohol* | 10.0 | 10.0 | 10.0 |
| Steareth-20** | 1.0 | 1.0 | 1.0 |
| Sodium laureth-2 sulfate | 0.35 | 0.7 | 1.4 |
| Ammonium hydroxide, 25% | 8.0 | 8.0 | 8.0 |
| Water | Qsp | Qsp | Qsp |

\* fatty alcohols according to the invention
\** non-ionic surfactants according to the invention First Set of Experimental Data—Influence of the Ratio of Fatty Alcohols to Non-Ionic Surfactants 8 hair colouring and/or bleaching compositions were obtained by mixing a developer and a tint component in a ratio 1:1 as shown below.

The ammonia smell released by the compositions upon application onto hair fibers was quantified by a panel of experts according to a scale ranging from 0 to 5, wherein 0=no ammonia odour detectable; 1=very weak ammonia odour; 2=weak ammonia odour; 3=moderate ammonia odour; 4=strong ammonia odour; 5=very strong ammonia odour. The average score for each of the compositions was calculated.

A composition was considered as providing a noticeably reduced odour smell, versus conventional hair colouring and/or bleaching ammonia-containing compositions, when an indicia of from 0 to 2 was obtained. Any composition ranked with an odour of 3 or above was considered as not providing a noticeably reduced ammonia odour.

Results:

| Mixed composition | T1 + D1 | T2 + D1 | T3 + D1 | T4 + D1 | T5 + D1 | T6 + D1 | T7 + D1 | T8 + D1 |
| --- | --- | --- | --- | --- | --- | --- | --- | --- |
| Total amount of fatty alcohols | 6.7 | 6.7 | 6.7 | 6.7 | 6.7 | 6.7 | 6.7 | 6.7 |
| Total amount of non-ionic surfactants | 5.4 | 4.4 | 3.4 | 2.9 | 2.4 | 1.9 | 1.4 | 0.9 |
| Ratio of fatty alcohols to non-ionic surfactants | 10:8.1 | 10:6.6 | 10:5.1 | 10:4.3 | 10:3.5 | 10:2.8 | 10:2.1 | 10:1.3 |
| Ammonia odour assessment score | 5 | 5 | 4 | 4 | 2 | 2 | 1 | 1 |

It can be seen from the results that a noticeable improvement in ammonia odour (scores of 2 and below) was detected for a ratio of fatty alcohol to non-ionic surfactant in the mixed composition above 10:4.3.

Second Set of Experimental Data-Influence of the Presence of Anionic Surfactant 4 hair colouring and/or bleaching compositions were obtained by mixing a developer and a tint component in a ratio 1:1 as shown below.

The ammonia smell released by the compositions upon application onto hair fibers was quantified by a panel of experts according to a scale ranging from 0 to 5, wherein 0=no ammonia odour detectable; 1=very weak ammonia odour; 2=weak ammonia odour; 3=moderate ammonia odour; 4=strong ammonia odour; 5=very strong ammonia odour. The average score for each of the compositions was calculated.

A composition was considered as providing a noticeably reduced odour smell, versus conventional hair colouring and/or bleaching ammonia-containing compositions, when an indicia of from 0 to 2 was obtained. Any composition ranked with an odour of 3 or above was considered as not providing a noticeably reduced ammonia odour.

Results:

|  | Mixed composition | | | |
| --- | --- | --- | --- | --- |
|  | T8 + D1 | T8 + 0.35% SLES + D1 | T8 + 0.7% SLES + D1 | T8 + 1.4% SLES + D1 |
| Total amount of fatty alcohols | 6.7 | 6.7 | 6.7 | 6.7 |
| Total amount of non-ionic surfactants | 0.9 | 0.9 | 0.9 | 0.9 |
| Ratio of fatty alcohols to non-ionic surfactants | 10:1.3 | 10:1.3 | 10:1.3 | 10:1.3 |
| Total amount of anionic surfactants | 0 | 0.175 | 0.35 | 0.7 |
| Ammonia odour assessment score | 1.5 | 2 | 3 | 4 |

It can be seen from the results that a noticeable improvement in ammonia odour (scores of 2 and below) was detected for compositions comprising a low amount of anionic surfactants.

The dimensions and values disclosed herein are not to be understood as being strictly limited to the exact numerical values recited. Instead, unless otherwise specified, each such dimension is intended to mean both the recited value and a functionally equivalent range surrounding that value. For example, a concentration disclosed as "1%" is intended to mean "about 1%".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colouring and/or bleaching composition comprising a first aqueous component and a second aqueous component, mixed prior to application onto hair, wherein:
   the first aqueous component comprises, in a cosmetically acceptable carrier:
      one or more oxidizing agent(s) and
      one or more fatty alcohol(s) and
      one or more non-ionic surfactant(s) other than fatty alcohol(s) and
   the second aqueous component comprises, in a cosmetically acceptable carrier:
      one or more alkalizing agent(s) selected from the group consisting of ammonia, its salts and mixtures thereof and
      one or more fatty alcohol(s) and
      one or more non-ionic surfactant(s) other than fatty alcohol(s),
   wherein the ratio between the total amount of fatty alcohol(s) and the total amount of non-ionic surfactant(s) other than fatty alcohol(s) comprised in the composition ranges from 10:0.1 to 10:4.2;
   wherein the composition comprises a total amount of fatty compound(s) selected from the group consisting of mineral oil, hydrocarbon oil, and mixtures thereof of less than 1% by total weight of the composition;
   wherein the composition comprises a total amount of anionic surfactant(s) of less than 0.5% by total weight of the composition;
   wherein the composition comprises a total amount of cationic surfactant(s) of less than 0.5% by total weight of the composition; wherein the non-ionic surfactant(s) is selected from the group consisting of polyoxyethylene C8 to C30 alkyl ethers; and
   wherein the fatty alcohol(s) is selected from the group consisting of linear and/or branched C14 to C30 fatty alcohols.

2. The composition according to claim 1, wherein the ratio between the total amount of fatty alcohol(s) and the total amount of non-ionic surfactant(s) other than fatty alcohol(s) comprised in the composition ranges from 10:0.1 to 10:4.1.

3. The composition according to claim 1, wherein the ratio between the total amount of fatty alcohol(s) and the total amount of non-ionic surfactant(s) other than fatty alcohol(s) comprised in the composition ranges from 10:0.1 to 10:4.

4. The composition according to claim 1, wherein the ratio between the total amount of fatty alcohol(s) and the total amount of non-ionic surfactant(s) other than fatty alcohol(s) comprised in the composition ranges from 10:0.5 to 10:3.5.

5. The composition according to claim 1, wherein the ratio between the total amount of fatty alcohol(s) and the total amount of non-ionic surfactant(s) other than fatty alcohol(s) comprised in the composition ranges from 10:1 to 10:2.

6. The composition according to claim 1, wherein the ratio between the total amount of fatty alcohol(s) and the total amount of non-ionic surfactant(s) other than fatty alcohol(s) comprised in the second aqueous component ranges from 10:0.1 to 10:4.1.

7. The composition according to claim 1, wherein the composition comprises a total amount of fatty compound(s) selected from the group consisting of mineral oil, hydrocarbon oil, and mixtures thereof of less than 0.5% by total weight of the composition.

8. The composition according to claim 1, wherein the composition is free of fatty compound(s) selected from the group consisting of mineral oil, hydrocarbon oil, and mixtures thereof.

9. The composition according to claim 1, wherein the first and the second components are mixed in a ratio ranging from 5:1 to 1:5.

10. The composition according to claim 1, wherein the composition comprises a total amount of surfactant(s) other than fatty alcohol(s) and non-ionic surfactant(s) of less than 1% by total weight of the composition.

11. The composition according to claim 1, wherein the composition comprises a total amount of polymer(s) selected from anionic and cationic polymers of less than 1% by total weight of the composition.

12. The composition according to claim 1, wherein the composition comprises a total amount of fatty alcohol(s) ranging from 0.5% to 20% by total weight of the composition.

13. The composition according to claim 1, wherein the composition comprises a total amount of non-ionic surfactant(s) other than fatty alcohol(s) ranging from 0.2% to 5% by total weight of the composition.

14. The composition according to claim 1, wherein the composition comprises a total amount of fatty alcohol(s) and non-ionic surfactant(s) ranging from 1% to 30% by total weight of the composition.

15. A kit for colouring and/or bleaching hair comprising a first and a second unit, comprising respectively the first and the second components, as defined in claim 1.

16. The kit according to claim 15, wherein it further comprises a third component selected from the group consisting of a conditioning composition, a pre-treatment composition, and/or a colour refresher composition.

17. A method of colouring and/or bleaching hair comprising applying onto hair a composition as defined in claim 1.

18. A method for colouring and/or bleaching hair comprising the steps of:
   providing a first component as defined in claim 1;
   providing a second component as defined in claim 1;
   mixing the first and the second components for obtaining a hair colouring and/or bleaching composition;
   applying the obtained composition onto hair.

19. The composition according to claim 1, wherein the fatty alcohol(s) is selected from the group consisting of cetyl alcohol, stearyl alcohol, cetearyl alcohol, behenyl alcohol, and mixtures thereof.

* * * * *